(12) United States Patent
Boss

(10) Patent No.: US 8,268,388 B1
(45) Date of Patent: Sep. 18, 2012

(54) METHOD TO INCORPORATE A FLUORESCENT INTERNAL STANDARD ON SUBSTRATES

(75) Inventor: Pamela A. Boss, San Diego, CA (US)

(73) Assignee: The United States of America as Represented by the Secretary of the Navy, Washington, DC (US)

( * ) Notice: Subject to any disclaimer, the term of this patent is extended or adjusted under 35 U.S.C. 154(b) by 1261 days.

(21) Appl. No.: 11/847,212

(22) Filed: Aug. 29, 2007

(51) Int. Cl.
*B05D 5/06* (2006.01)
*B32B 5/16* (2006.01)
*G01N 21/17* (2006.01)

(52) U.S. Cl. ......... 427/167; 427/169; 428/407; 436/172

(58) Field of Classification Search .................. 428/401, 428/402, 403, 404, 405, 406, 407, 408, 409; 427/169; 436/525, 526, 172, 805
See application file for complete search history.

(56) References Cited

U.S. PATENT DOCUMENTS

| | | | |
|---|---|---|---|
| 6,242,264 B1 * | 6/2001 | Natan et al. | 436/171 |
| 6,514,767 B1 * | 2/2003 | Natan | 436/166 |
| 7,588,827 B2 * | 9/2009 | Nie et al. | 428/403 |
| 2003/0228682 A1 * | 12/2003 | Lakowicz et al. | 435/287.2 |
| 2004/0058458 A1 * | 3/2004 | Anker et al. | 436/526 |
| 2004/0121337 A1 * | 6/2004 | Deans et al. | 435/6 |
| 2008/0085566 A1 * | 4/2008 | Swager et al. | 436/172 |

OTHER PUBLICATIONS

Shibata et al, Preparation of Silica Microspheres containing Ag Nanoparticles, Journal of Sol-Gel Science and Technology, 11, 1998, 279-287.*

Boyd et al., Photoinduced luminescence from the noble metals and its enhancement on roughened surfaces, Physical Review B, 33, 12, 1986, 7923-7936.*

Yang et al., Fluorescent Porous Polymer Films as TNT Chemosensors: Electronic and Structural Effects, J. Am. Chem Soc., vol. 120, No. 46, 1998.*

* cited by examiner

*Primary Examiner* — Michael Cleveland
*Assistant Examiner* — Francisco Tschen
(74) *Attorney, Agent, or Firm* — Arthur K. Samora; Kyle Eppele

(57) ABSTRACT

A Method to Incorporate a Fluorescent Internal Standard on Substrates (NC#098329). The method includes providing a substrate, operatively coupling internal standard particles to the substrate, forming an insulating buffer layer over the internal standard particles and the substrate, and forming a sensing polymer layer over the insulating buffer layer.

19 Claims, 6 Drawing Sheets

Side View (Note: FIGS 2A-2E are NOT drawn to scale)

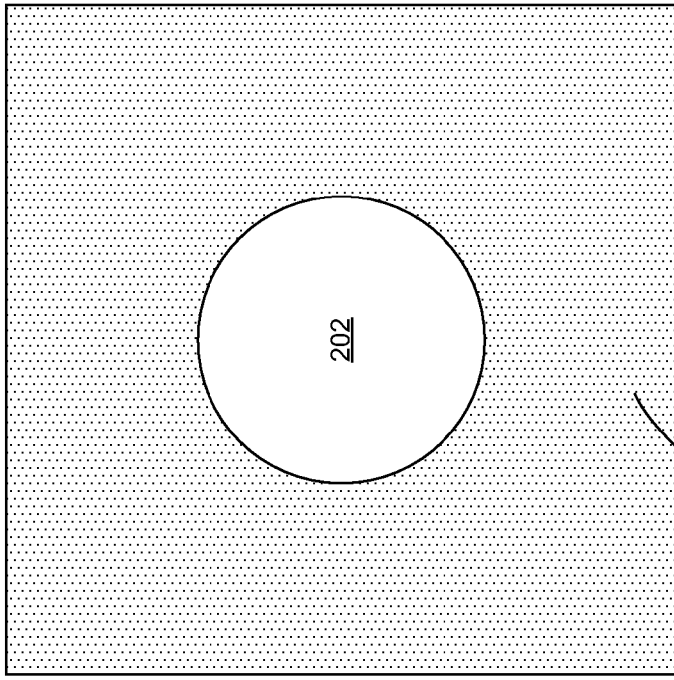
FIG. 2B
Side View
(Note: FIGS 2A-2E are NOT drawn to scale)
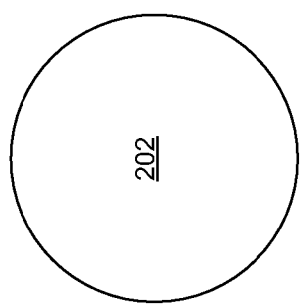
FIG. 2A
Side View
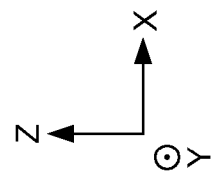

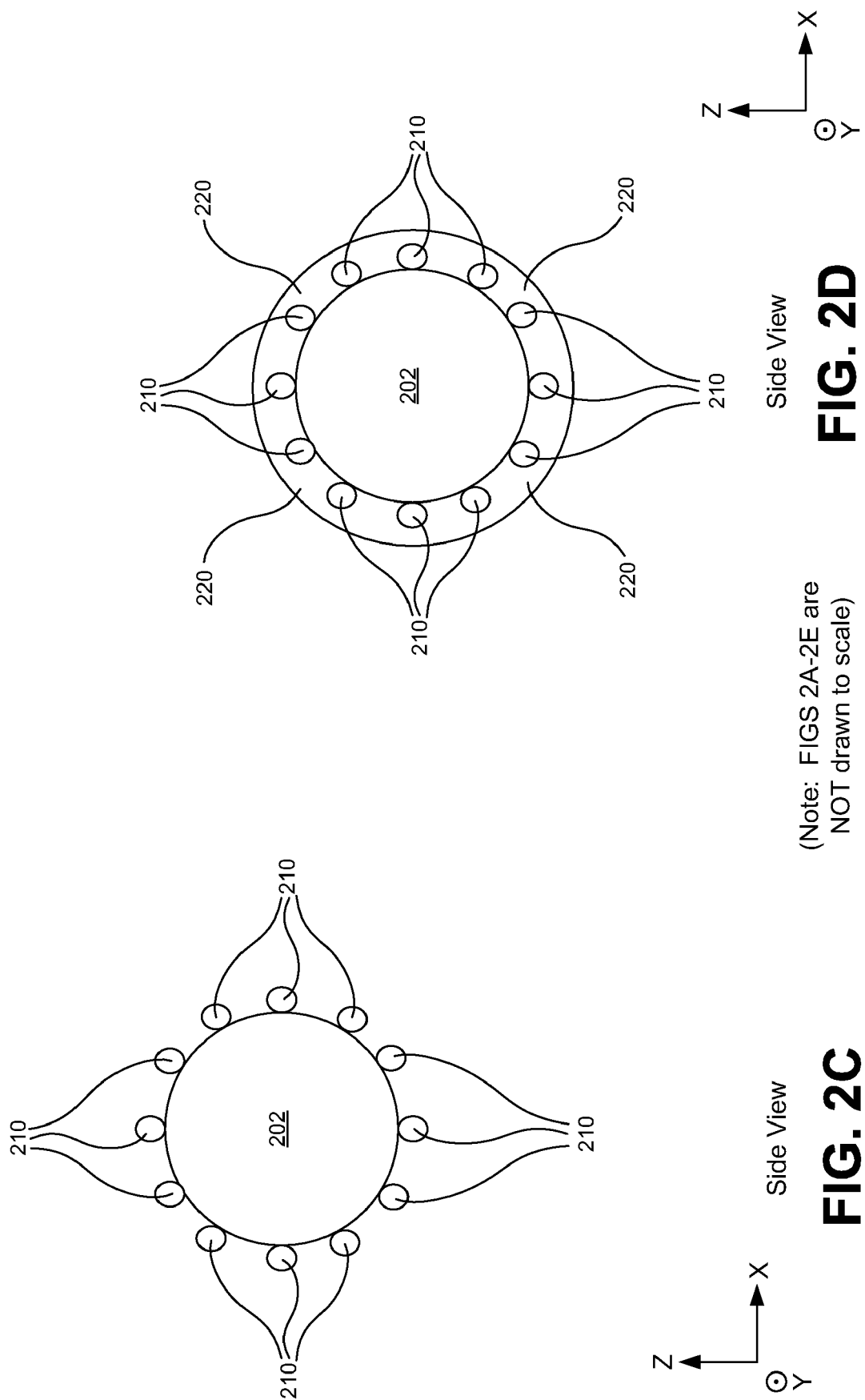

Side View

Side View

Top View

Front View

US 8,268,388 B1

METHOD TO INCORPORATE A FLUORESCENT INTERNAL STANDARD ON SUBSTRATES

FEDERALLY SPONSORED RESEARCH AND DEVELOPMENT

This invention (Navy Case No. 098329) is assigned to the United States Government and is available for licensing for commercial purposes. Licensing and technical inquiries may be directed to the Office of Research and Technical Applications, Space and Naval Warfare Systems Center, San Diego, Code 2112, San Diego, Calif., 92152; voice (619) 553-2778; email T2@spawar.navy.mil. Reference Navy Case Number 098329.

BACKGROUND OF THE INVENTION

The Method to Incorporate a Fluorescent Internal Standard on Substrates is generally in the field of internal standards for analytes.

Typical analyte response detectors that do not use an internal standard can provide false positive results due to varying environmental conditions. Internal standards for analytes are used to provide a known amount of a compound that is different from the analyte to provide a baseline that fluctuates with the analyte when environmental conditions vary.

A need exists for incorporating fluorescent internal standards on substrates.

BRIEF DESCRIPTION OF THE DRAWINGS

FIG. 2A is a cross-sectional side view of one embodiment of a fluorescent internal standard on substrates in an intermediate stage of manufacture.

FIG. 2B is a cross-sectional side view of one embodiment of a fluorescent internal standard on substrates in an intermediate stage of manufacture.

FIG. 2C is a cross-sectional side view of one embodiment of a fluorescent internal standard on substrates in an intermediate stage of manufacture.

FIG. 2D is a cross-sectional side view of one embodiment of a fluorescent internal standard on substrates in an intermediate stage of manufacture.

DETAILED DESCRIPTION OF THE INVENTION

Described herein is Method to Incorporate a Fluorescent Internal Standard on Substrates.

Definitions

The following acronyms are used herein:
Acronym(s):
3-APTMS—3-aminopropyltrimethoxysilane
3-MPTMS—3-mercaptopropyltrimethoxysilane
FIS—Fluorescent Internal Standard
FISOS—Fluorescent Internal Standard on Substrate
ISCP—Internal Standard Colloidal Particles
ISP—Internal Standard Particles
TEOS—Tetraethylorthosilicate
TMOS—Tetramethyloorthosilicate
TNT—Trinitrotoluene The Method to Incorporate a Fluorescent Internal Standard on Substrates includes procedures of providing a substrate; operatively coupling internal standard particles (ISP) to the outside surface of the substrate; forming an insulating buffer layer over the ISP and substrate; and forming a sensing polymer layer over the insulating buffer layer. In one embodiment, the substrate comprises glass. In one embodiment, the substrate comprises glass spheres. In one embodiment, the ISP comprises quantum dots. In one embodiment, the ISP comprises internal standard colloidal particles (ISCP). In one embodiment, the ISCP comprises a metal selected from the group consisting of platinum, gold, silver or a combination of these metals. In one embodiment, the insulating buffer layer comprises glass. In one embodiment, the sensing polymer layer comprises a fluorescent polymer layer.

Figure 1:
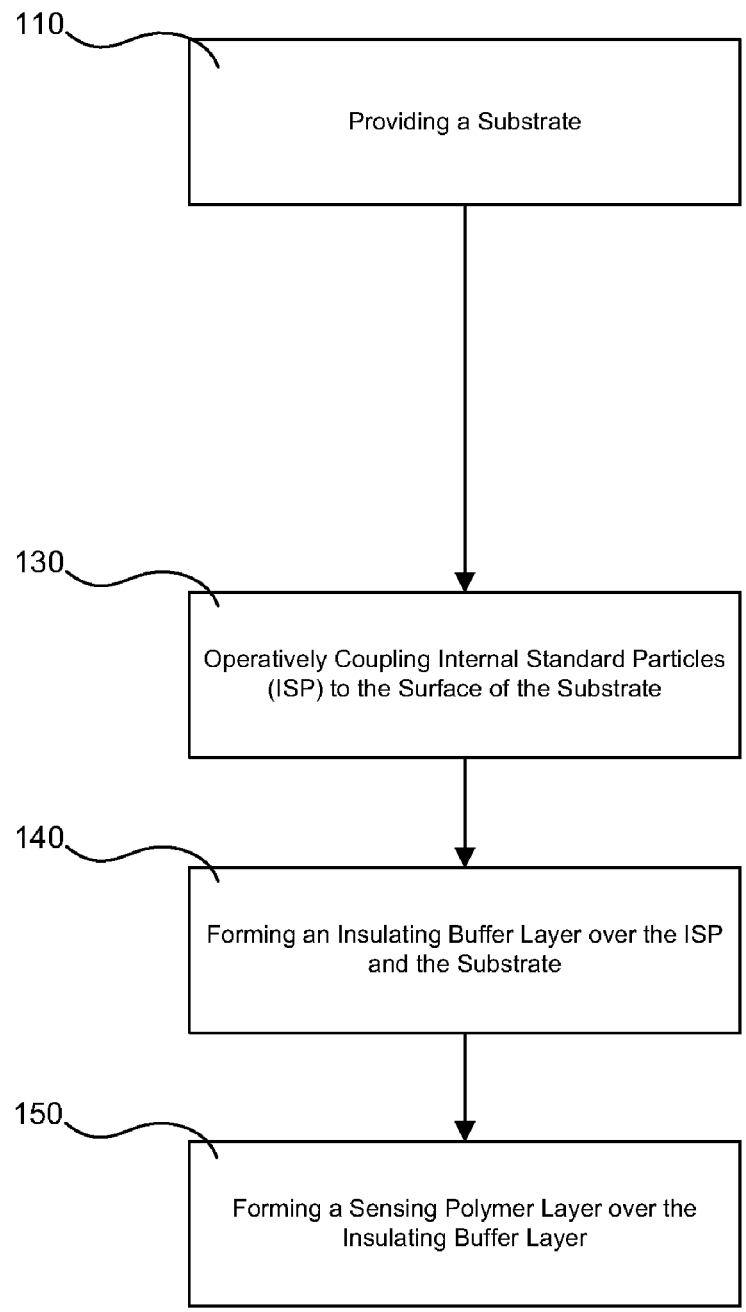
FIG. 1 is a flowchart illustrating exemplary process procedures taken to manufacture one embodiment of a fluorescent internal standard on substrate.

FIG. 1 is a flowchart illustrating exemplary process procedures taken to manufacture one embodiment of a fluorescent internal standard on substrate (FISOS). Certain details and features have been left out of flowchart 100 of FIG. 1 that are apparent to a person of ordinary skill in the art. For example, a procedure may consist of one or more sub-procedures or may involve specialized equipment or materials, as known in the art. While procedures 110 through 150 shown in flowchart 100 are sufficient to describe one embodiment, other embodiments may utilize procedures different from those shown in flowchart 100.

Figure 2E:
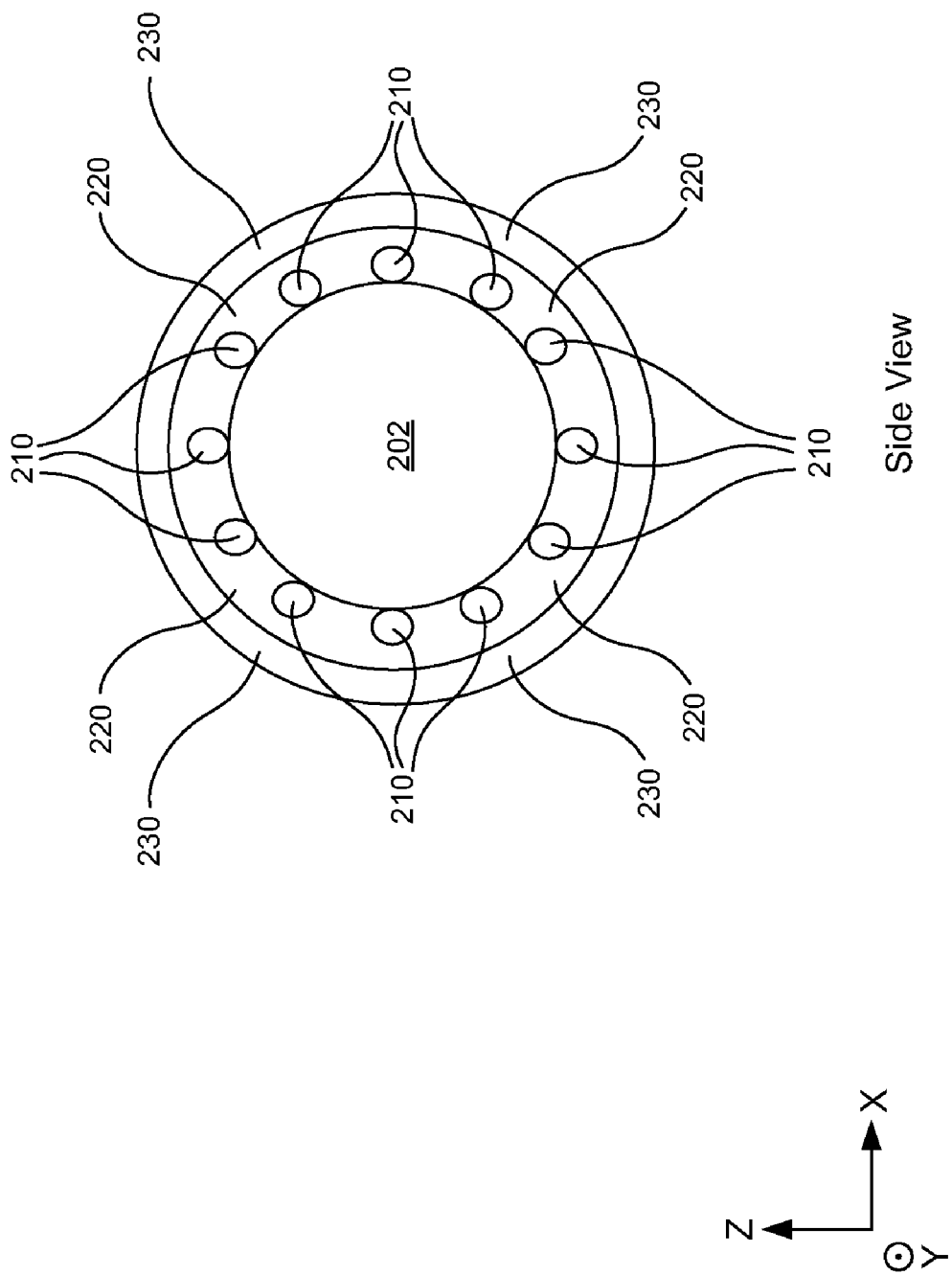
FIG. 2E is a cross-sectional side view of one embodiment of a fluorescent internal standard on substrates in an intermediate stage of manufacture.

FIGS. 2A-2E are cross-sectional side views of some of the features of an exemplary fluorescent internal standard on substrate in intermediate stages of fabrication. These fabrication stages are described in greater detail below in relation to flowchart 100 of FIG. 1 and flowchart 400 of FIG. 4. FIG. 2A is a cross-sectional side view of one embodiment of a fluorescent internal standard on substrates in an intermediate stage of manufacture.

Referring to FIGS. 1 and 2A, at procedure 110 in flowchart 100, the method provides substrate 202. In one embodiment, the method provides a glass substrate. In one embodiment, the method provides a glass sphere. In one embodiment, the method provides a glass slide. In one embodiment, the method provides a glass tube. In one embodiment, the method provides a plastic material having appropriate functional groups to bind internal standard particles. In one embodiment, the method provides a silica sphere. In one embodiment, the method provides a silica sphere having a diameter between approximately 0.19 micrometers and approximately 5 micrometers. Those skilled in the art shall recognize that internal standard particles of various sizes can be used without departing from the scope or spirit of the method to incorporate a fluorescent internal standard on substrates. Other exemplary glass substrates include glass polygons, cubes and tetrahedrons. After procedure 110, the method proceeds to procedure 130.

Referring to FIGS. 1 and 2C, at procedure 130 in flowchart 100, the method operatively couples internal standard particles 210 to the surface of substrate 202. ISP 210 comprise robust particles that fluoresce in red light wavelengths such as metal colloidal particles and quantum dots (i.e., semiconductor nanocrystals). Metal colloidal particles and quantum dots exhibit large quantum efficiencies, size-dependent emission wavelengths and photobleach resistance. In one embodiment, ISP 210 comprises quantum dots. In one embodiment, ISP 210 comprises quantum dots coated with amine and carboxyl groups. In one embodiment, ISP 210 comprises silver colloidal particles. In one embodiment, ISP 210 comprises gold colloidal particles. In one embodiment, ISP 210 comprises platinum colloidal particles. In one embodiment, ISP 210 comprises colloidal particles comprising a combination of at least two of the following metals to the surface of substrate 202: silver, gold and platinum.

In one embodiment of procedure 130 using a glass substrate for substrate 202 and metal colloidal particles for ISP 210, the method operatively couples ISP 210 to the surface of substrate 202 by coating substrate 202 in a colloidal group binder and situating substrate 202 in a solution of colloidal particles. In one embodiment of procedure 130, the method operatively couples ISP 210 to the surface of substrate 202 by reacting the surface of substrate 202 with 3-aminopropyltrimethoxysilane (3-APTMS) and situating substrate 202 in a solution of colloidal particles. Thus, the siloxane groups of the 3-APTMS bind to the glass and the amine groups of the 3-APTMS immobilize/bind ISP 210 to the surface of substrate 202.

In one embodiment of procedure 130, the method operatively couples ISP 210 to the surface of substrate 202 by exposing substrate 202 to colloidal particles using vapor deposition techniques such as chemical vapor deposition and physical vapor deposition. After procedure 130, the method proceeds to procedure 140.

Referring to FIGS. 1 and 2D, at procedure 140 in flowchart 100, the method forms insulating buffer layer 220 over ISP 210 and substrate 202. Insulating buffer layer 220 comprises a material that is transparent to red light wavelengths. In one embodiment, insulating buffer layer 220 comprises glass. In one embodiment, insulating buffer layer 220 comprises a plastic material. Exemplary methods of forming insulating buffer layer 220 over ISP 210 and substrate 202 include reacting silicate with a functionalized trimethoxysilane to form a glass shell.

In one embodiment of procedure 140 using a glass substrate for substrate 202 and metal colloidal particles for ISP 210, the method forms insulating buffer layer 220 over ISP 210 and substrate 202 by reacting ISP 210 with 3-APTMS or 3-mercaptopropyltrimethoxysilane (3-MPTMS) and adding one of the following: sodium silicate, tetraethylorthosilicate (TEOS), tetramethyloorthosilicate (TMOS) or a combination of two or more of the above. Thus, the amine/thiol groups of 3-APTMS/3-MPTMS bind to the surface of ISP 210 and the silicates of sodium silicate, TEOS or TMOS react with the trimethoxysilane of 3-APTMS/3-MPTMS to form a glass shell around ISP 210 and substrate 202. After procedure 140, the method proceeds to procedure 150.

Referring to FIGS. 1 and 2E, at procedure 150 in flowchart 100, the method forms sensing polymer layer 230 over insulating buffer layer 220. Sensing polymer layer 230 comprises a material that is capable of fluorescing. In one embodiment, sensing polymer layer 230 comprises a pentiptycene-based polymer. Exemplary methods of forming sensing polymer layer 230 over insulating buffer layer 220 includes coating via solution or vapor deposition to chemically bind sensing polymer layer 230 to insulating buffer layer 220. After Procedure 150, the method ends.

Figure 3:
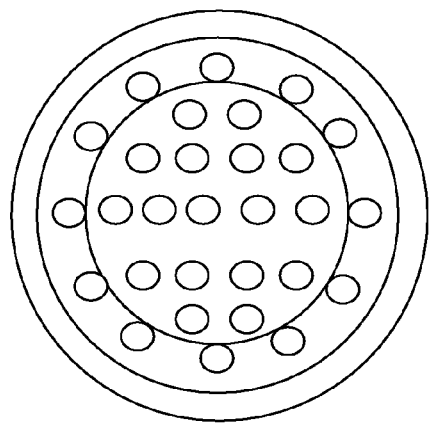
FIG. 3 is a side, top and front view of one embodiment of a fluorescent internal standard on substrate.
Figure 3:
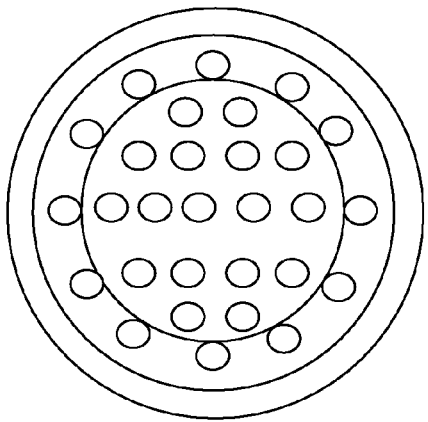
Figure 3:
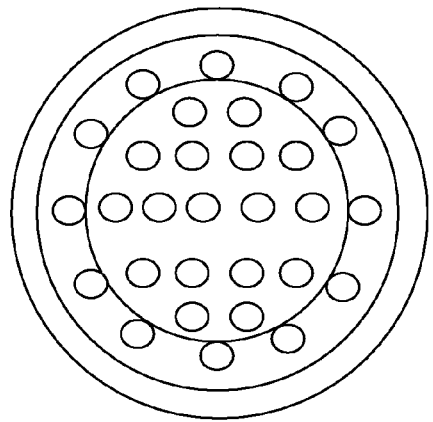

FIG. 3 is a side, top and front view of one embodiment of a fluorescent internal standard on substrate. As shown in FIG. 3, the FISOS comprise a glass sphere having ISP (e.g., gold particles) operatively coupled to the surface of the glass sphere. The glass sphere and ISP are covered by an insulating buffer layer and a sensing polymer layer.

Figure 4:
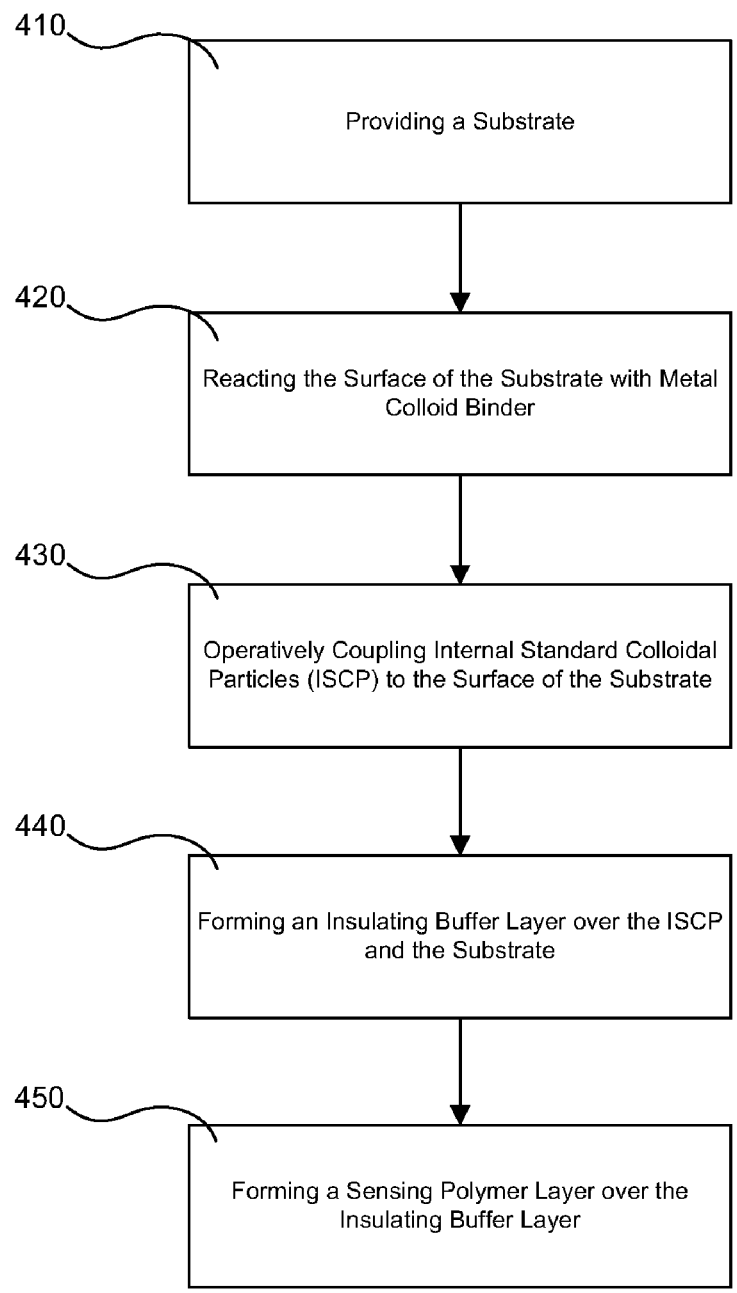
FIG. 4 is a flowchart illustrating exemplary process procedures taken to manufacture one embodiment of a fluorescent internal standard on substrate.

FIG. 4 is a flowchart illustrating exemplary process procedures taken to manufacture one embodiment of a fluorescent internal standard on substrate. Certain details and features have been left out of flowchart 400 of FIG. 4 that are apparent to a person of ordinary skill in the art. For example, a procedure may consist of one or more sub-procedures or may involve specialized equipment or materials, as known in the art. While procedures 410 through 450 shown in flowchart 400 are sufficient to describe one embodiment, other embodiments may utilize procedures different from those shown in flowchart 400. FIG. 4 is substantially similar to FIG. 1, and thus, some procedures are not described again in detail.

Referring to FIGS. 4 and 2A, at procedure 410 in flowchart 400, the method provides substrate 202. In this embodiment, substrate 202 comprises a glass sphere having a diameter between approximately 0.19 micrometers and approximately 5 micrometers. After procedure 410, the method proceeds to procedure 420.

Referring to FIGS. 4 and 2B, at procedure 420 in flowchart 100, the method reacts the surface of substrate 202 with metal colloidal binder 204. As shown in FIG. 2B, metal colloidal binder 204 is represented by a plurality of dots within a square chamber. In this embodiment, metal colloidal binder 204 comprises 3-APTMS. Thus, the siloxane portion of 3-APTMS binds to the glass surface of substrate 202. After procedure 420, the method proceeds to procedure 430.

Referring to FIGS. 4 and 2C, at procedure 430 in flowchart 400, the method operatively couples internal standard particles 210 to the surface of substrate 202. In this embodiment, ISP 210 comprises gold colloidal particles. The method at procedure 430 immerses substrate 202 in a solution of gold colloidal particles, which are immobilized by the amine groups of the 3-APTMS to the surface of substrate 202. After procedure 430, the method proceeds to procedure 440.

An exemplary method of preparing a solution of gold colloidal particles is now described. Place 100 mL of an aqueous 0.01% HAuCl4 solution in a round bottom flask with a stir bar and condenser column. Boil solution with constant stirring. Add 1% sodium citrate. In one embodiment, 0.42 mL of 1% sodium citrate is added, which yields gold particles averaging 98 nanometers in diameter. In one embodiment, 0.933 mL of 1% sodium citrate is added, which yields gold particles averaging 60 nanometers in diameter. Reflux for 40 minutes. Centrifuge until the final volume is decreased by approximately 33 times. Thus, a 100 mL volume is decreased to approximately 3 mL.

An exemplary method of preparing a solution of silver colloidal particles is now described. Place 18 mg silver nitrate and 200 mL of water in a round bottom flask with a stir bar and condenser column. Boil solution with constant stirring. Add 4 mL of 1% sodium citrate with constant stirring. Reflux for 60 minutes. Centrifuge until the final volume is decreased by approximately 33 times. Thus, a 200 mL volume is decreased to approximately 6 mL.

Referring to FIGS. 4 and 2D, at procedure 440 in flowchart 400, the method forms insulating buffer layer 220 over ISP 210 and substrate 202. In this embodiment, insulating buffer layer 220 comprises glass. In one embodiment of procedure 440, the method forms insulating buffer layer 220 over ISP 210 and substrate 202 by reacting ISP 210 with 3-MPTMS and adding sodium silicate to form a glass shell around ISP 210 and substrate 202. After procedure 440, the method proceeds to procedure 450.

Referring to FIGS. 4 and 2E, at procedure 450 in flowchart 400, the method forms sensing polymer layer 230 over insulating buffer layer 220. In this embodiment, sensing polymer layer 230 comprises pentiptycene-based polymers. After Procedure 450, the method ends.

To provide a better understanding of the operation of fluorescent internal standard on substrates, an exemplary operation is now described. A plurality of FISOS comprising spherical substrates designed to react with Trinitrotoluene (TNT) are dispersed in the cargo area of an airplane. A multiple light wavelength source (e.g., red light lantern) interrogates the cargo area, which causes the plurality of FISOS to fluoresce. A detector receives the fluorescent light and determines the response by the fluorescent internal standard and the fluorescent polymer coating. In this example, the internal standard fluoresces in the red and the sensing polymer fluoresces at a different wavelength (e.g., more in the blue light spectrum). In the case of the TNT-selective polymer, binding to TNT causes a decrease in the signal. The internal standard is used to determine whether or not a real change in the signal from the sensing layer has occurred. The detector compares the two responses and provides either a negative or positive result for the presence of TNT.

What is claimed:

1. A method for incorporating a fluorescent internal standard within a quenching fluorescent analyte response detector, comprising the steps of:
    providing a substrate;
    operatively coupling fluorescent internal standard particles that fluoresce at a first wavelength to said substrate;
    forming an insulating buffer layer over said fluorescent internal standard particles and said substrate; and,
    forming a sensing polymer layer that fluoresce at a second wavelength over said insulating buffer layer, said second wavelength being different than said first wavelength.

2. The method of claim 1, wherein said substrate is a glass substrate.

3. The method of claim 1, wherein said substrate is a glass sphere.

4. The method of claim 1, wherein said fluorescent internal standard particles comprise internal standard colloidal particles.

5. The method of claim 1, wherein said fluorescent internal standard particles comprise quantum dots.

6. The method of claim 1, wherein said fluorescent internal standard particles comprise internal standard gold colloidal particles.

7. The method of claim 1, wherein said fluorescent internal standard particles comprise internal standard silver colloidal particles.

8. The method of claim 1, wherein said insulating buffer layer comprises a glass shell.

9. The method of claim 1, wherein said sensing polymer layer comprises a pentiptycene-based polymer.

10. The method of claim 1, wherein said procedure of operatively coupling fluorescent internal standard particles to said substrate comprises:
    coating said substrate in a colloidal group binder;
    situating said substrate in a solution of colloidal particles.

11. The method of claim 1, wherein said procedure of operatively coupling fluorescent internal standard particles to said substrate comprises:
    reacting said substrate with 3-APTMS;
    situating said substrate in a solution of colloidal particles.

12. The method of claim 1, wherein said procedure of forming said insulating buffer layer over said fluorescent internal standard particles and said substrate comprises:
    reacting said fluorescent internal standard particles with 3-APTMS;
    adding sodium silicate to said fluorescent said internal standard particles.

13. The method of claim 1, wherein said procedure of forming said insulating buffer layer over said fluorescent internal standard particles and said substrate comprises:
    reacting said fluorescent internal standard particles with 3-MPTMS;
    adding sodium silicate to said fluorescent internal standard particles.

14. A method for incorporating a fluorescent internal standard internal to a quenching fluorescent analyte response detector, comprising:
    providing a substrate;
    reacting said substrate with a metal colloid binder;
    operatively coupling fluorescent internal standard particles that fluoresce at a first wavelength to said substrate;
    forming an insulating buffer layer over said fluorescent internal standard particles and said substrate;
    forming a sensing polymer layer that fluoresces at a second wavelength over said insulating buffer layer, said second wavelength being different than said first wavelength.

15. The method of claim 14, wherein said procedure of providing said substrate comprises providing a glass sphere.

16. The method of claim 14, wherein said procedure of providing said substrate comprises providing a glass sphere having a diameter between approximately 0.19 micrometers and approximately 5 micrometers.

17. The method of claim 14, wherein said procedure of reacting said substrate with said metal colloid binder comprises reacting said substrate with 3-APTMS.

18. The method of claim 14, wherein said procedure of operatively coupling said fluorescent internal standard particles to said substrate comprises immersing said substrate in a solution of gold colloidal particles.

19. The method of claim 14, wherein said procedure of forming said insulating buffer layer over said fluorescent internal standard particles and said substrate comprises:
    a reacting said fluorescent internal standard particles with 3-MPTMS;
    a adding sodium silicate to said fluorescent internal standard particles.

* * * * *